United States Patent [19]
de los Angeles Rey et al.

[11] Patent Number: 6,080,878
[45] Date of Patent: Jun. 27, 2000

[54] METHOD OF PREPARING 16-DEHYDRO VITAMIN D COMPOUNDS

[75] Inventors: Maria de los Angeles Rey; Antonio Mouriño; Ana Fernandez-Gacio; Yagamare Fall, all of Santiago de Compostela, Spain; Sebastianus J. Halkes, Weesp, Netherlands; Koen M. Halkes, Weesp, Netherlands; Jan-Paul van de Velde, Weesp, Netherlands; Jan Zorgdrager, Weesp, Netherlands

[73] Assignee: Duphar International Research B.V., Weesp, Netherlands

[21] Appl. No.: 09/067,903

[22] Filed: Apr. 29, 1998

[30] Foreign Application Priority Data

May 2, 1997 [EP] European Pat. Off. ............ 97201334

[51] Int. Cl.⁷ .................................................. C07C 401/00
[52] U.S. Cl. .............................................................. 552/563
[58] Field of Search .............................. 552/563; 514/167

[56] References Cited

U.S. PATENT DOCUMENTS 5,384,314  1/1995  Doran et al. ............................ 514/167

FOREIGN PATENT DOCUMENTS

| 0325279A | 7/1989 | European Pat. Off. . |
| 398217 A1 | 11/1990 | European Pat. Off. . |
| 0599114A | 6/1994 | European Pat. Off. . |
| 0646576A | 4/1995 | European Pat. Off. . |
| 0654476A | 5/1995 | European Pat. Off. . |
| 0717034 | 6/1996 | European Pat. Off. . |

OTHER PUBLICATIONS

Advanced Organic Chemistry: Reactions, Mechanisms, and Structure, Jerry March, pp. 873–874.
Chemical Abstracts, vol. 124, No. 5, Jan. 29, 1996.

*Primary Examiner*—Jose' G. Dees
*Assistant Examiner*—Alton Pryor
*Attorney, Agent, or Firm*—Stevens, Davis, Miller & Mosher, L.L.P.

[57] ABSTRACT

The invention relates to a new method of preparing 16-dehydro vitamin D compounds having formula I

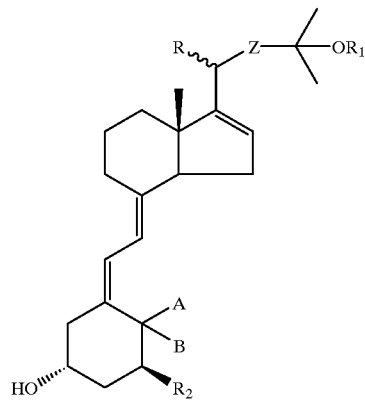

wherein:
R has the epi-configuration or the normal configuration and represents straight or branched $C_{1-6}$-alkyl, $C_{2-6}$-alkenyl, $C_{3-6}$-cycloalkyl, or an aromatic group optionally substituted with halogen, $C_{1-3}$-alkyl or alkoxy,
Z is a saturated or unsaturated straight hydrocarbon group or oxahydrocarbon group containing 3–6 C-atoms which may be substituted with OH, F, alkyl ($C_{1-3}$) or cycloalkyl ($C_{3-5}$),
$R_1$ is hydrogen or an hydroxy protecting group,
$R_2$ is hydrogen or hydroxy, and
A and B represent hydrogen or methyl, or together form the methylene group, to the new compounds having this formula and to new intermediates obtainable according to this process.

1 Claim, No Drawings

METHOD OF PREPARING 16-DEHYDRO VITAMIN D COMPOUNDS

The invention relates to a new method of preparing 16-dehydro vitamin D compounds, to a group of new 16-dehydro vitamin D compounds and to their use in pharmacology.

It is generally known, that vitamin D compounds or vitamin D related compounds ("vitamin D compounds") have a strong biological activity and may be used in all those cases in which problems with the calcium metabolism play a part. A few years ago it was found that various active vitamin D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications, and for diagnostic purposes.

It is therefore of the utmost importance to have the disposal of an arsenal of active vitamin D compounds for the above various application fields so as to be able to make the best possible choice of a vitamin D compound for the application in view.

According to the method of the present invention 16-dehydro vitamin D compounds of the general formula I

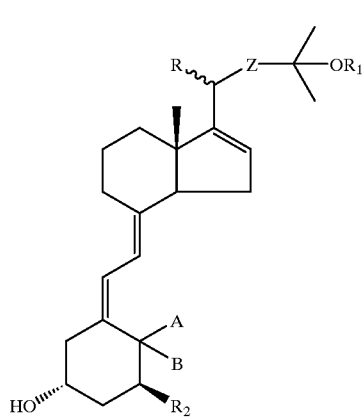

(I)

wherein:
R has the epi-configuration or the normal configuration and represents straight or branched $C_{1-6}$-alkyl, $C_{2-6}$-alkenyl, $C_{3-6}$-cycloalkyl, or an aromatic group optionally substituted with halogen, $C_{1-3}$-alkyl or alkoxy,
Z is a saturated or unsaturated straight hydrocarbon group or oxahydrocarbon group containing 3–6 C-atoms which may be substituted with OH, F, alkyl ($C_{1-3}$) or cycloalkyl ($C_{3-5}$),
$R_1$ is hydrogen or an hydroxy protecting group,
$R_2$ is hydrogen or hydroxy, and
A and B represent hydrogen or methyl, or together form the methylene group, can easily be obtained in good yield.

The compounds as defined above having formula I wherein the symbols have the meanings given above, with the proviso that when R is methyl and Z is a straight hydrocarbon group containing 3 C-atoms this group R has the epi-configuration, are new compounds.

The new modified vitamin D compounds of the invention, presented by the general formula I are valuable substances. The biological results indicate that these compounds are promising as biologically active substances and may be used in all above-mentioned pharmacotherapeutic indications, more in particular for the treatment of osteoporosis, renal osteodystrophy, osteomalacia, skin disorders such as psoriasis (and other hyperproliferative skin diseases), eczema and dermatitis, myopathy, leukaemia, breast and colon cancer, osteosarcomas, squamous cell carcinomas, melanoma, certain immunological disorders, and transplant rejections. For this application, the new compounds of the invention may be incorporated, in effective amounts, in pharmaceutical compositions, comprising in addition pharmaceutical acceptable carriers and auxiliary substances. Furthermore, the new vitamin D compounds of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion. The new vitamin D compounds may also be used for diagnostic purposes.

Preferred compounds are vitamin D compounds of the general formula I, wherein Z is the group $(CH_2)_3$, $R_1$ is hydrogen, $R_2$ is hydroxy, and R has the epi-configuration and represents $C_{1-4}$-alkyl, cyclopropyl or phenyl, and A+B represent methylene.

The invention relates to a new method of preparing 16-dehydro vitamin D compounds of the above formula I by reacting a compound of the general formula II

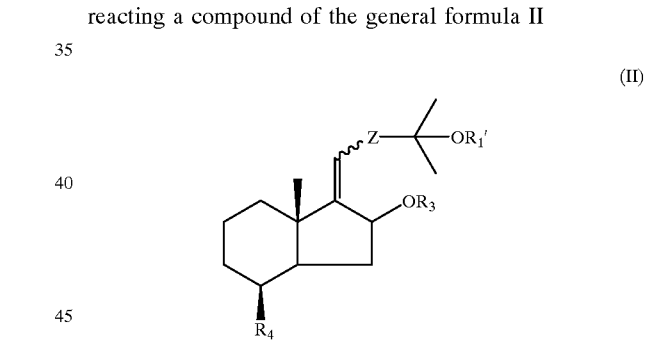

(II)

wherein Z has the above meaning, $R'_1$ is a hydroxy protecting group, $R_3$ is a carbamate group or a pivalate group, and $R_4$ is a protected hydroxy group or a group of the formula III

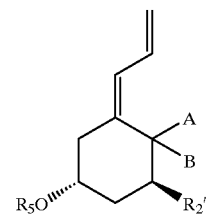

(III)

wherein A and B have the above meaning, $R_5$ is a hydroxy protecting group, and $R'_2$ is hydrogen or a hydroxy protecting group, with a suitable cuprate reagent for introducing group R to produce a compound of the formula IV

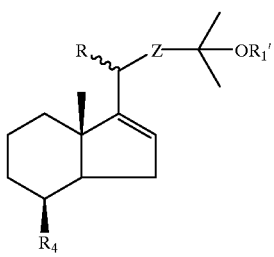

(IV)

wherein R, R'$_1$, Z and R4 have the above meaning, followed by converting the obtained compound having formula IV into a compound having formula I in a manner known per se, as illustrated in the Examples.

Hydroxy groups in the above intermediates or reactants may be protected by a reaction with a suitable esterification or etherification agent. A suitable esterification agent is an alkylchlorocarbonate having 2 to 5 carbon atoms, or an aromatic carboxylic acid or saturated aliphatic carboxylic acid having 1 to 4 carbon atoms such as benzoic, or a derivative of such acids suitable for the esterification reaction. In order to protect the hydroxy group in the form of an ether, in principle any etherification agent known for this purpose is suitable: for example, a methoxymethylating agent (such as methoxymethylchloride), a trialkylsilylimidazole, a trialkylsilylhalide, a trialkylsilyltriflate, a diphenylalkylsilylhalide, or a diphenylalkylsilyltriflate, or a derivative thereof, the alkyl groups of which have 1 to 6 carbon atoms. Particularly suitable for this purpose are trimethylsilylchloride, tert.-butyldimethylsilylchloride, dimethyl-(1,1,2-trimethylpropyl)-silylchloride, tert.-butyidimethylsilyl triflate, or trimethylsilyl-imidazole, because these etherification agents readily react with the hydroxy group(s) to be protected to form an ether function, which on the one hand is sufficiently stable under the conditions of the reaction or reactions in view, but on the other hand can easily be removed [deprotection] to recover the original hydroxy group; tert.-butyidimethylsilylchloride or triflate is to be preferred, because the tert.-butyidimethylsilyl group has been found to be excellently suitable as a protective group.

The starting compounds having formula II can be obtained by converting a corresponding compound wherein the group OR$_3$ is hydrogen (which compounds are described in EP. 0717034) in a manner known per se into the desired compound 11 (see Example 3).

The obtained compounds having formula IV wherein R$_4$ is a protected hydroxy group can be converted into a compound having formula I in a manner known per se by deprotecting group R$_4$ and oxidising the deprotected hydroxy group to the keto group, and converting the obtained keto-compound (a) with a Wittig reagent of the general formula V

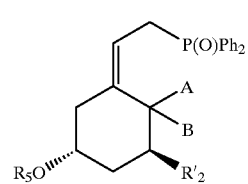

(V)

wherein A, B, R$_5$ and R'$_2$ have the above meanings; or (b) after enolization and derivatisation of the enolic hydroxy group, with an enyne compound of the formula VI

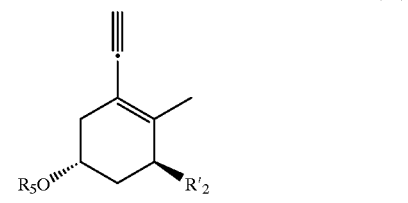

(VI)

wherein R'$_2$ and R$_5$ have the above meaning, followed by hydrogenation and isomerization to produce a compound of formula I wherein A+B form the methylene group;

followed by deprotection of hydroxy group(s).

The enolic hydroxy group in compound VI is preferably derivatized by reaction with N-phenyltriflimide to produce the corresponding triflate.

The conversion of a compound having formula II into a compound of the formula IV is carried out with a so-called cuprate reagent. The cuprate reagent to be used depends on the meaning of group R in the desired compound having formula I as appears from the following Scheme A (when R$_4$ is protected hydroxy) and Scheme B (when R$_4$ is a group of formula III)

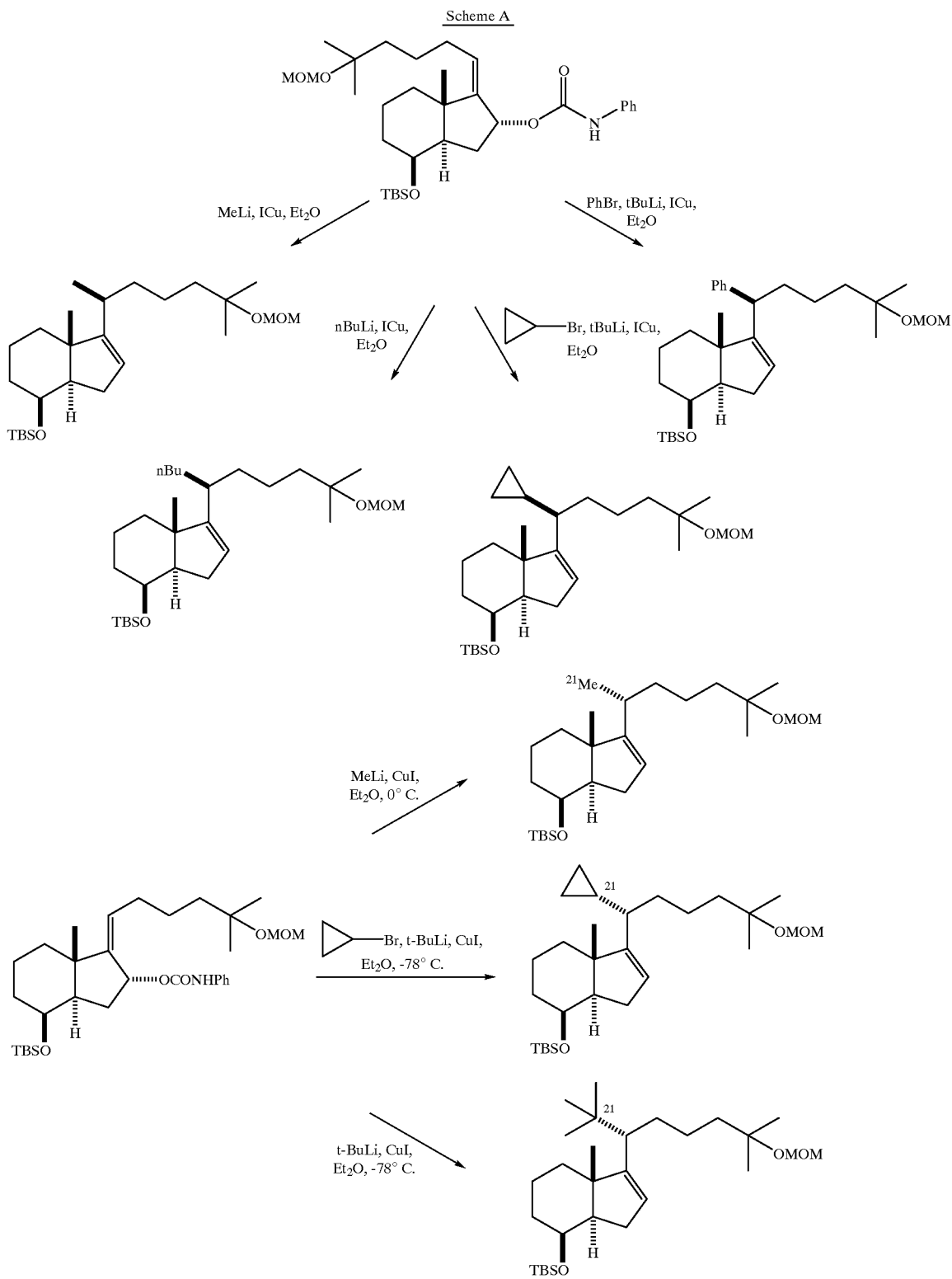

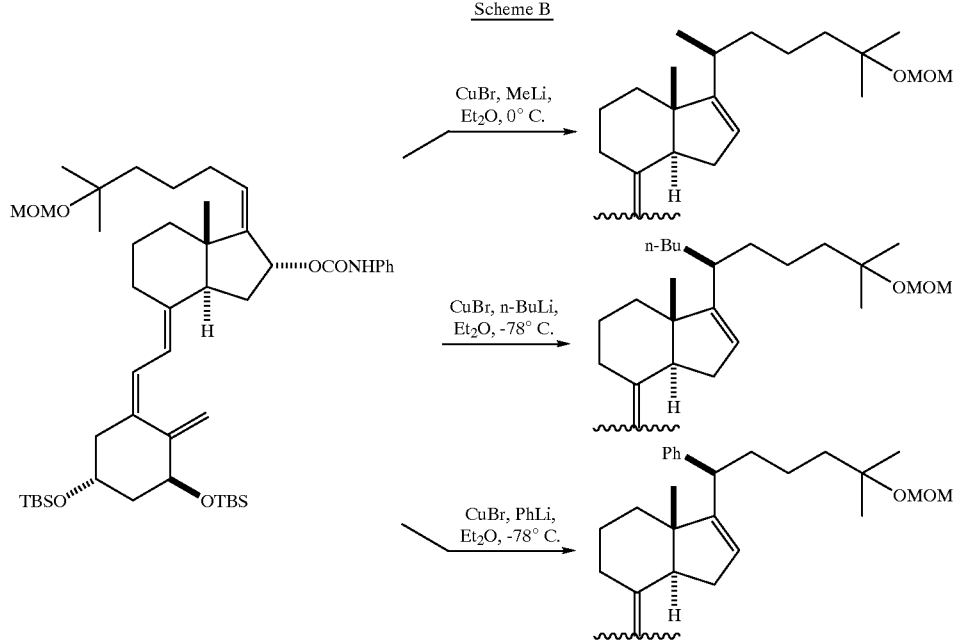
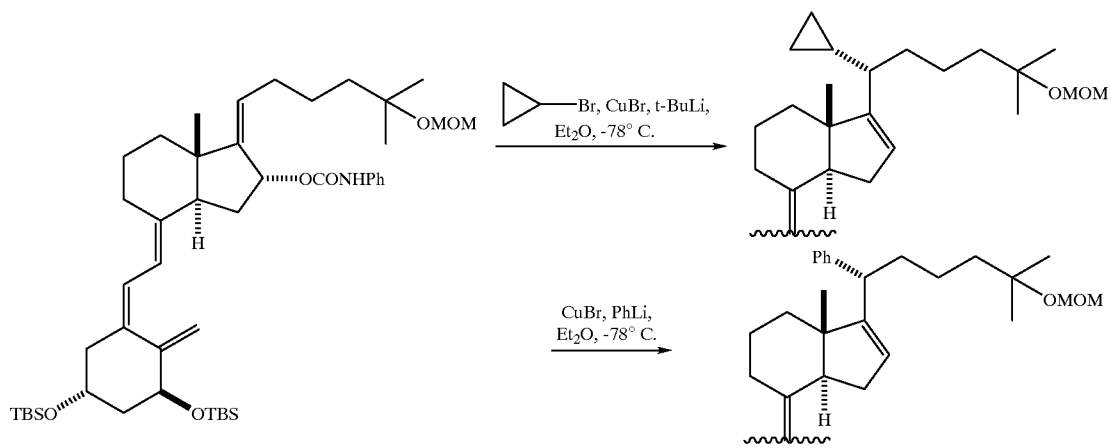
50
The conversion of a compound of formula IV obtained according to Scheme A, after selective deprotection and oxidation of the hydroxy group to the keto group, with a Wittig reagent is indicated in Scheme C:

Scheme C
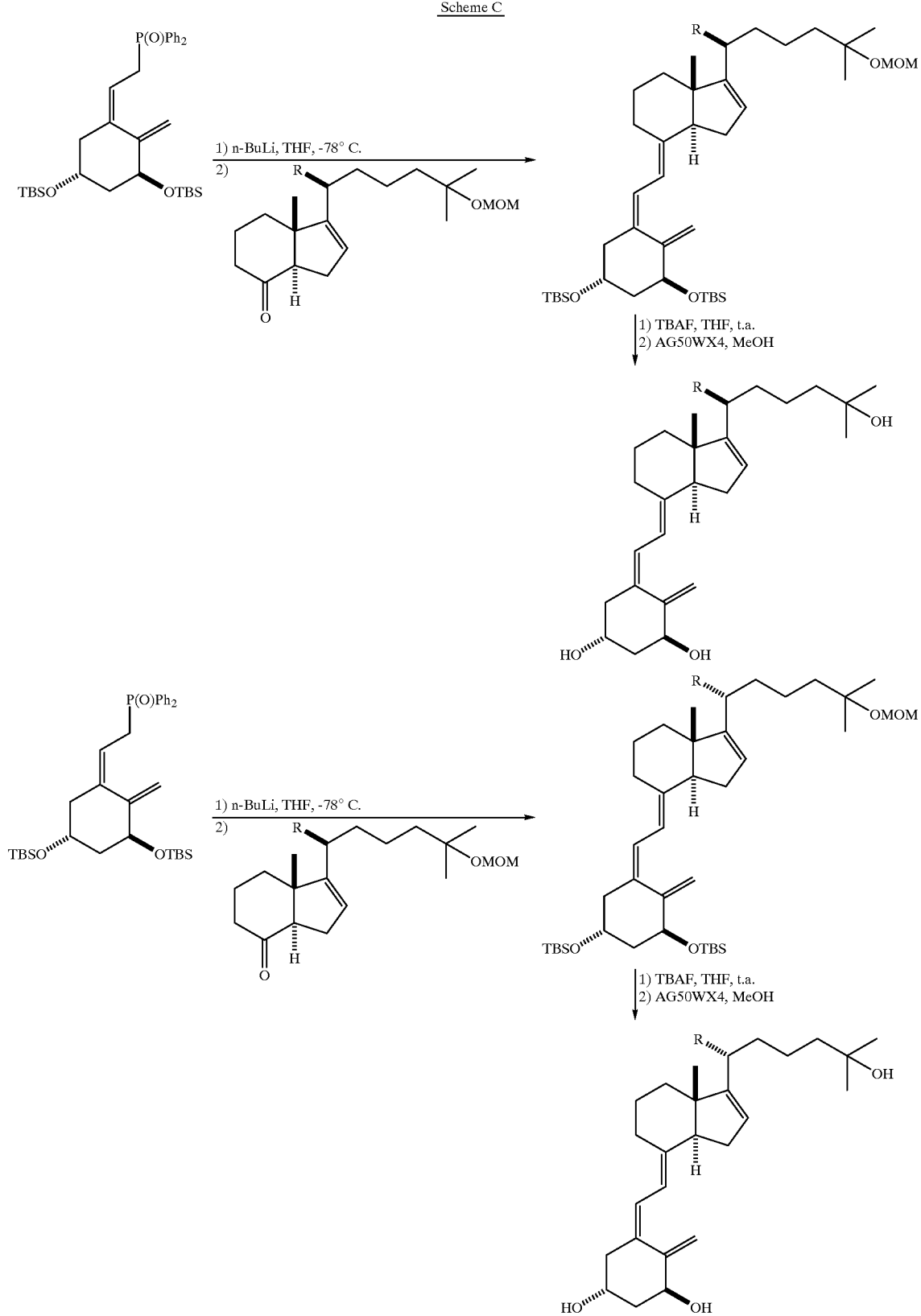

EXAMPLE 1
preparation of compound 2 from compound 1.

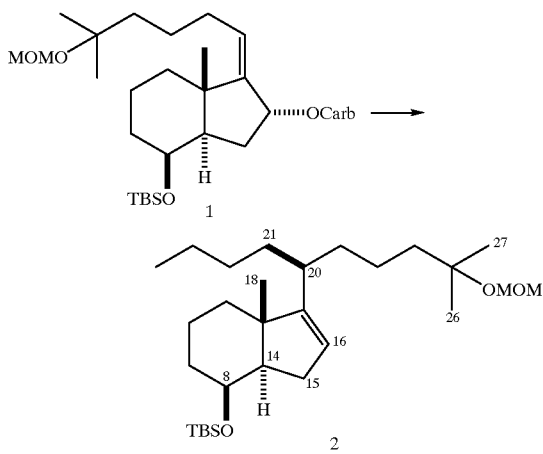

To a cooled (−78° C.) suspension of 379 mg of CuI (1.99 mmol) in 8 ml of dry Et$_2$O under an argon atmosphere, was added 1.59 ml of a 2.5 M solution of n-BuLi in hexanes (3.97 mmol). After stirring for 1 hr, 150 mg of 1 (0.26 mmol) in 4 ml dry Et$_2$O was added. The reaction mixture was allowed to reach room temperature and stirring was continued for 12 hrs in the dark. The reaction was quenched by the addition of 10 ml of a saturated NH$_4$Cl solution. After separation of the layers, the aqueous layer was extracted with Et$_2$O (3×10 ml). The combined organic layers were washed with 15 ml of a saturated NaHCO$_3$ solution, dried, filtered and concentrated at reduced pressure. The residue was purified by flash chromatography (Eluent 1% EtOAC/hexane) resulting in 113.1 mg of 2 as a colourless oil (88%, Rf=0.76; 20% EtOAc/hexane).

$^1$H-NMR (CDCl$_3$, 250 MHz, δ): 5.22 (1H, t, J=1.1 Hz, H-16), 4.69 (2H, s, OCH$_2$O), 4.06 (1H, m, H-8), 3.38 (3H, s, MeO), 2.22 (1H, m, H-14), 1.98–1.59 (3H, m, H-15 and H-20), 1.18 (6H, s, Me-26 and Me-27), 0.98 (3H, s, Me-18), 0.85 (11H, s, t-BuSi and CH$_2$-21), 0.04 (6H, s, Me$_2$Si)

According to a similar procedure the following compounds of the formula IV wherein Z is (CH$_2$)$_3$ and R$_1$'= MOM have been prepared:

a) R=epi-phenyl; R$_4$=TBSO $^1$H-NMR (CDCl$_3$, 250 MHz, δ): 7.28–7.12 (5H, m, Ar), 5.49 (1H, t, J=1.5 Hz, H-16), 4.65 (2H, s, OCH$_2$O), 4.07 (1H, m, H-8), 3.29 (3H, s, MeO), 3.23 (1H, t, J=7.6 Hz, H-20), 2.25 (1H, m, H-14), 1.84 (2H, m, H-15), 1.14 (6H, s, Me-26 and Me-27), 0.84 (9H, s, t-BuSi), 0.68 (3H, s, Me-18), 0.045 (6H, s, Me$_2$Si).

b)=epi-cloppropyl; R$_4$=TBSO $^1$H-NMR (CDCl$_3$, 250 MHz, δ): 5.37 (1H, t, J=1.1 Hz, H-16), 4.67 (2H, s, OCH$_2$O), 4.07 (1H, m, H-8), 3.33 (3H, s, MeO), 2.23 (1H, m, H-14), 1.90–1.54 (3H, m, H-15 and H-20), 1.18 (6H, s, Me-26 and Me-27), 0.99 (3H, s, Me-18), 0.86 (9H, s, t-BuSi), 0.80 (1H, m, H-21), 0.49 (1H, m, CH$_2$-cyclopropyl), 0.36 (1H, m, CH$_2$-cyclopropyl), 0.10 (1H, m, CH$_2$-cyclopropyl), 0.00 (6H, s, Me$_2$Si), −0.08 (1H, m, CH$_2$-cyclopropyl).

c) R=epi-methyl; R$_4$=TBSO $^1$H-NMR (CDCl$_3$, 250 MHz, δ): 5.29 (1H, t, J=1.2 Hz, H-16), 4.70 (2H, s, OCH$_2$O), 4.09 (1H, m, H-8), 3.36 (3H, s, MeO), 2.24–2.05 (4H, m, H-20, H-15 and H-14), 1.19 (6H, s, Me-26 and Me-27), 1.03 (3H, d, J=6.8 Hz, Me-21), 1.02 (3H, s, Me-18), 0.85 (9H, s, t-BuSi), 0.01 (6H, s, Me$_2$Si).

d) R=normal-methyl; R$_4$=TBSO $^1$H-NMR (CDCl$_3$, 250 MHz, δ): 5.25 (1H, t, J=1.5 Hz, H-16), 4.70 (2H, s, OCH$_2$O), 4.08 (1H, d, J=2.2 Hz, H-8), 3.36 (3H, s, MeO), 2.22–1.90 (4H, m, H-14, H-15 and H-20), 1.20 (6H, s, Me-26 and Me-27), 1.01 (3H, s, Me-18), 0.97 (3H, d, J=6.8 Hz, Me-21), 0.89 (9H, s, t-BuSi), 0.03 (3H, S, Me$_2$Si), 0.02 (3H, s, Me$_2$Si).

e) R=normal-tert.butyl; R$_4$=TBSO $^1$H-NMR (CDCl$_3$, 250 MHz, δ): 5.32 (1H, t, J=1.1 Hz, H-16), 4.68 (2H, s, OCH$_2$O), −4.09 (1H, m, H-8), 3.37 (3H, s, MeO), 2.23 (1H, m, H-14), 1.98–1.61 (3H, m, H-15 and H-20), 1.19 (6H, s, Me-26 and Me-27), 1.04 (3H, s, Me-18), 0.88 (9H, s, t-Bu), 0.86 (9H, s, t-BuSi), 0.01 (6H, s, Me$_2$Si).

f) R=normal-cyclopropyl; R$_4$=TBSO $^1$H-NMR (CDCl$_3$, 250 MHz, δ): 5.31 (1H, t, J=1.5 Hz, H-16), 4.69 (2H, s, OCH$_2$O), 4.08 (1H, m, H-8), 3.36 (3H, s, MeO), 2.25 (1H, m, H-14), 1.90-1.62 (3H, m, H-15 and H-20), 1.20 (6H, s, Me-26 and Me-27), 1.06 (3H, s, Me-18), 0.89 (9H, s, t-BuSi), 0.88–0.35 (5H, m, cyclopropyl), 0.026 (6H, s, Me$_2$Si).

g) R=epi-methyl; R$_4$=

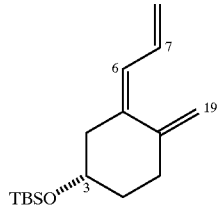

$^1$H-NMR (CD$_2$Cl$_2$, 250 MHz, δ): 6.16, 6.09 (2H, AB, J=11.2 Hz, H-6 and H-7), 5.30 (1H, S broad, H-16), 5.01 (1H, d, J=1.2 Hz, H-19$_E$), 4.76 (1H, d, J=1.6 Hz, H-19$_Z$), 4.63 (2H, s, OCH$_2$O), 3.84 (1H, m, H-3), 3.29 (3H, S, MeO), 2.80 (1H, dd, 1=12.5 Hz and 4.4 Hz, H-14), 1.16 (6H, s, Me-26 and Me-27), 1.02 (3H, d, J=6.9 Hz, Me-21), 0.87 (9H, s, t-BuSi), 0.67 (3H, s, Me-18), 0.05 (3 H, s, MeSi), 0.04 (3H, s, MeSi).

h) R=epi-n.butyl; R$_4$=

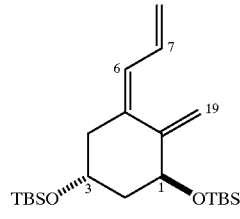

$^1$H-NMR (CD$_2$Cl$_2$, 250 MHz, δ): 6.25, 6.10 (2H, AB, J=11.1 Hz, H-6 and H-7), 5.27 (1H, s broad, H-16), 5.19 (1H, s broad, H-19$_E$), 4.85 (1H, d, J=2.5 Hz, H-19$_Z$), 4.63(2H, s, OCH$_2$O), 4.37 (1H, m, H-1), 4.18 (1H, m, H-3), 3.29 (3H, s, MeO), 2.81(1H, m, H-14), 1.15 (6H, s, Me-26 and Me-27), 0.87 (2H, m, H-21), 0.86 (18H, s, 2 t-BuSi), 0.62 (3H, s, Me-18), 0.06 (3H, s, MeSi), 0.05 (3 H, s, MeSi), -0.10 (3H, s, MeSi), -0.14 (3H, s, MeSi).

i) R=normal-cyclopropyl; $R_4$=

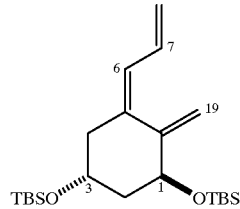

$^1$H-NMR (CDCl$_3$, 250 MHz, δ): 6.26,6.12 (2H, AB, J=11.7 Hz, H-6 and H-7), 5.35 (1H, m, H-16), 5.19 (1H, s broad, H-19$_E$), 4.86 (1H, s broad, H-19$_Z$), 4.63 (2H, s, OCH$_2$O), 4.39 (1H, m, H-i), 4.19 (1H, m, H-3), 3.28 (3H, S, MeO), 2.80 (1H, m, H-14), 1.14 (6H, s, Me-26 and Me-27), 0.88 (18H, s, 2 t-BuSi), 0.80 (1H, m, H-21), 0.72 (3H, s, Me-18), 0.45 (2H, m, CH$_2$-cyclopropyl), 0.09 (2H, m, CH$_2$-cyclopropyl), 0.06 (6H, s, Me$_2$Si), 0.057 (6H, s, Me$_2$Si).

j) R=normal-phenyl; $R_4$=

$^1$H-NMR (CDCl$_3$, 250 MHz, δ): 7.28–7.14 (5H, m, Ar), 6.23, 6.12 (2H, AB, J=11.1 Hz, H-6 and H-7), 5.56 (1H, m, H-16), 5.20 (1H, S broad, H-19$_E$), 4.87 (1H, s broad, H-19$_Z$), 4.60 (2H, s, OCH$_2$O), 4.39 (1H, m, H-1), 4.19 (1H, m, H-3), 3.24 (3H, S, MeO), 2.75 (1H, m, H-14), 1.12 (6H, S, Me-26 and Me-27), 0.89 (9H, s, t-BuSi), 0.87 (9H, s, t-BuSi), 0.70 (3H, s, Me-18), 0.08 (6H, s, Me$_2$Si), 0.07 (6H, S, Me$_2$Si).

EXAMPLE 2

(i) preparation of compound 4 from compound 3

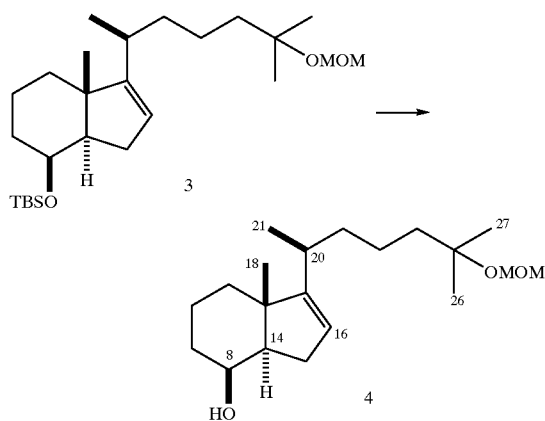

To a solution of 70 mg of 3 (0.16 mmol) in 0.5 ml dry THF under an argon atmosphere, was added 0.79 ml of a 1M solution of TBAF in THF (0.79 mmol). The mixture was heated to reflux and stirring was continued for 12 hrs. The reaction was quenched by the addition of 4 ml of a saturated NaHCO$_3$ solution. After separation of the layers, the aqueous layer was extracted with Et$_2$O (3×10 ml). The combined organic layers were dried, filtered and concentrated at reduced pressure. The residue was purified by flash chromatography (Eluent 10% EtOAC/hexane) resulting in 50.6 mg of 4 as a colourless oil (98%, Rf=0.53; 20% EtOAc/hexane).

$^1$H-NMR (CDCl$_3$, 250 MHz, δ): 5.30 (1H, t, J=1.2 Hz, H-16), 4.66 (2H, s, OCH$_2$O), 4.09 (1H, m, H-8), 3.33 (3H, s, MeO), 2.28–2.05 (4H, m, H-20, H-15 and H-14), 1.17 (6H, s, Me-26 and Me-27), 1.03 (3H, d, J=6.8 Hz, Me-21), 1.02 (3H, s, Me-18).

(ii) preparation of compound 5 fom compound 4

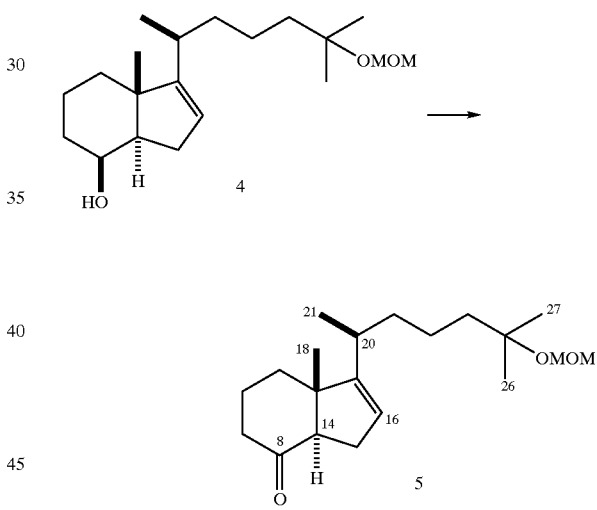

To a solution of 34 mg of 4 (0.105 mmol) in 1.5 ml dry CH$_2$Cl$_2$ under an argon atmosphere, was added 109 mg of PDC (0.29 mmol). The mixture was stirred for 6 hrs. The reaction mixture was filtered over Celite and the residue was washed with CH$_2$Cl$_2$. The filtrate was concentrated at reduced pressure and the remaining residue was purified by flash chromatography (Eluent 10% EtOAC/hexane) resulting in 32.8 mg of 5 as a colourless oil (97%, Rf=0.62; 20% EtOAc/hexane).

$^1$H-NMR (CDCl$_3$, 250 MHz, δ): 5.28 (1H, t, J=1.2 Hz, H-16), 4.68 (2H, s, OCH$_2$O), 3.35 (3H, s, MeO), 2.80 (1H, dd, J=10.6 Hz and 6.4 Hz, H-14), 2.46–2.24 (5H, m, H-9, H-20 and H-15), 1.19 (6H, s, Me-26 and Me-27), 1.05 (3H, d, J=6.8 Hz, Me-21), 0.80 (3H, s, Me-18).

(iii) preparation of compound 6 from compound 5.

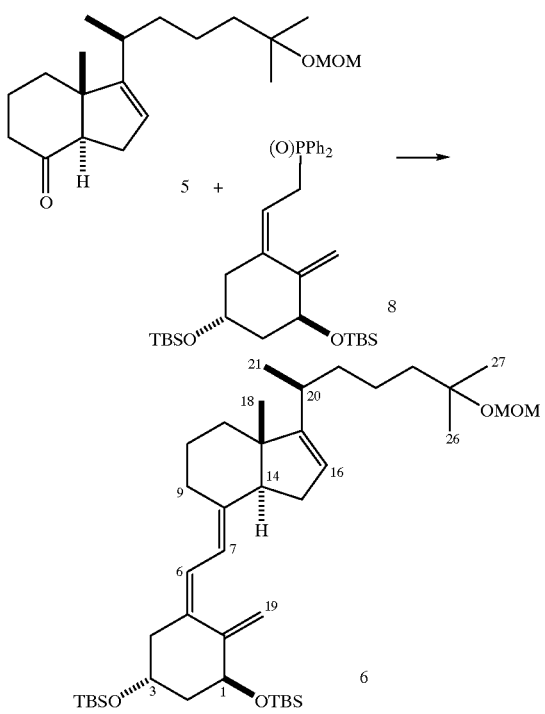

To a cooled (−78° C.) solution of 126 mg of compound 8 (0.216 mmol) in 3 ml of dry THF under an argon atmosphere, was added 0.10 ml of a 2.1 M solution of n-BuLi in hexanes (0.216 mmol). After stirring for 1 hr, 35 mg of 5 (0.11 mmol) in 1.6 ml dry THF was added. The reaction mixture was stirred for 12 hrs at −78° C. in the dark and was allowed to reach a temperature of −40° C. in 2 hrs. The reaction was quenched by the addition of 5 ml of water. After separation of the layers, the aqueous layer was extracted with Et$_2$O (3×10 ml). The combined organic layers were washed with 10 ml of a saturated NaCl solution, dried, filtered and concentrated at reduced pressure. The residue was purified by flash chromatography (Eluent 1% EtOAC/hexanes) resulting in 68 mg of 6 as a white solid (92%, Rf=0.77; 20% EtOAc/hexanes).

(iv) preparation of compound 7 from compound 6.

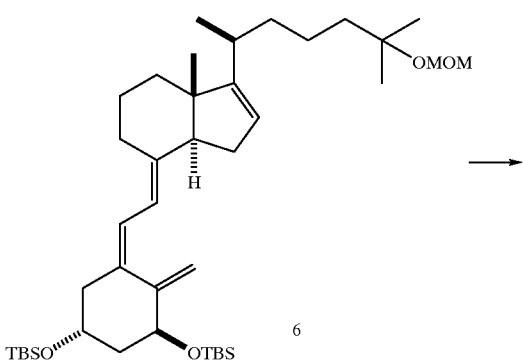

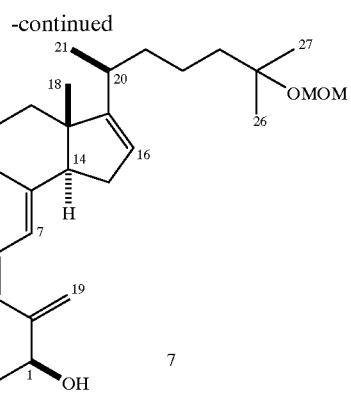

To a solution of 31 mg of 3 (0.045 mmol) in 0.3 ml dry THF under an argon atmosphere, was added 0.84 ml of a 1M solution of TBAF in THF (0.84 mmol). The mixture was stirred in the dark at room temperature for 12 hrs. The reaction was quenched by the addition of 5 ml of a saturated NH$_4$Cl solution. After separation of the layers, the aqueous layer was extracted with Et$_2$O (3×10 ml). The combined organic layers were dried, filtered and concentrated at reduced pressure. The residue was used directly in the following reaction.

(v) preparation of compound 9 from compound 7

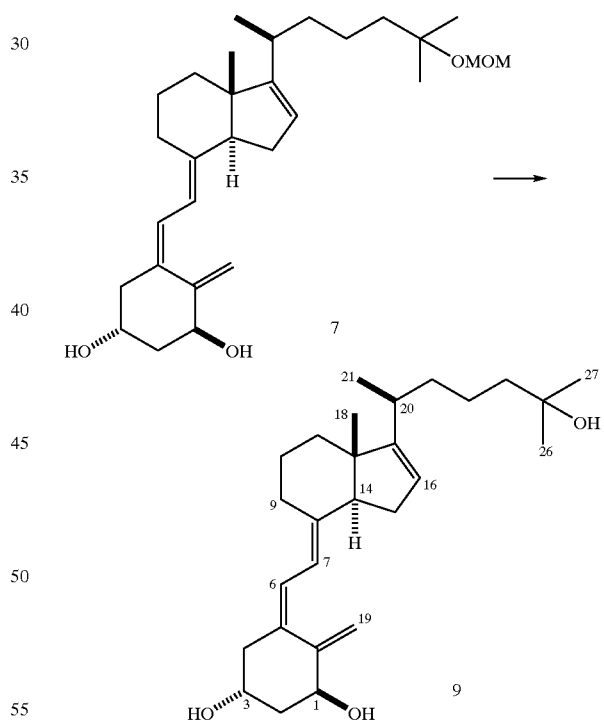

Compound 7 was dissolved in 3 ml of dry MeOH under an argon atmosphere. An amount of 450 mg cationic resin AG50W-X4 (washed with 3×10 ml MeOH and dried in vacuo).was added and the mixture was stirred for 5 hrs in the dark. The cationic resin was removed by filtration and washed with dry Et$_2$O (4×10 ml). The filtrate was concentrated at reduced pressure and the remaining residue was purified by flash chromatography (Eluent 50% EtOAC/hexane) resulting in 16 mg of 9 as a white solid (88%, Rf=0.35; 50% EtOAc/hexane).

$^1$H-NMR (CDCl$_3$, 250 MHz, δ): 6.35, 6.09 (2H, AB, J=11.1 Hz, H-6 and H-7), 5.30 (1H, s broad, H-16), 5.27 (1H, s broad, H-19$_E$), 4.90 (1H, s broad, H-19$_Z$), 4.38 (1H, m, H-1), 4.15 (1H, m, H-3), 2.81 (1H, dd, m, H-14), 1.15 (6H, s, Me-26 and Me-27), 1.03 (3H, d, J=6.8 Hz, Me-21), 0.69 (3H, s, Me-18).

According to the process steps i-v the following compounds of formula I wherein Z is (CH$_2$)$_3$, R$_1$=H, A+B= methylene and R$_2$=OH have been prepared:

a) R=epi-n.butyl $^1$H-NMR (CDCl$_3$, 250 MHz, δ): 6.35, 6.10 (2H, AB, J=11.1 Hz, H-6 and H-7), 5.30 (2H, s broad, H-16 and H-19$_E$), 4.96 (1H, s broad, H-19$_Z$), 4.37 (1H, m, H-1), 4.16 (1H, m, H-3), 2.81 (1H, m, H-14), 1.15 (6H, s, Me-26 and Me-27), 0.85 (2H, m, H-21), 0.67 (3H, s, Me-18).

b) R=epi-phenyl $^1$H-NMR (CDCl$_3$, 250 MHz, δ): 7.26–7.13 (5H, m, Ph), 6.30, 6.03 (2H, AB, J=11. 1 Hz, H 6 and H-7), 5.56 (1H, s broad, H-16), 5.26 (1H, s broad, H-19$_E$), 4.91 (1H, s broad, H-19$_Z$), 4.35 (1H, m, H-1), 4.13 (1H, m, H-3), 3.22 (1H, t, J=7.5 Hz, H-20), 2.79 (1H, m, H-14), 1.08 (6H, s, Me-26 and Me-27), 0.20 (3 H, s, Me-18).

c) R=epi-cyclopropyl $^1$H-NMR (CDCl$_3$, 250 MHz, δ): 6.35, 6.10 (2H, AB, J=11.3 Hz, H-6 and H-7), 5.40 (1H, s broad, H-16), 5.30 (1H, s broad, H-19$_E$), 4.96 (1H, s broad, H-19$_Z$), 4.38 (1H, m, H-1), 4.16 (1H, m, H-3), 2.78 (1H, m, H-14), 1.15 (6H, s, Me-26 and Me-27), 0.84 (1H, m, H-21), 0.69 (3H, s, Me-18), 0.56 (1H, m, CH$_2$-cyclopropyl), 0.40 (1H, m, CH$_2$-Cyclopropyl), 0.17 (1H, m, CH$_2$-cyclopropyl), -0.02 (1H, m, CH$_2$-cyclopropyl).

d) R=normal-cyclopropyl $^1$H-NMR (CDCl$_3$, 250 MHz, δ): 6.35, 6.10 (2H, AB, 1=11.7 Hz, H-6 and H-7), 5.34 (1H, m, H-16), 5.29 (1H, s broad, H-19$_E$), 4.96 (1H, s broad, H-19z), 4.38 (1H, m, H-1), 4.18 (1H, m, H-3), 2.83 (1H, m, H-14), 1.14 (6H, s, Me-26 and Me-27), 0.86 (1H, m, H-21), 0.73 (3H, s, Me-18), 0.42 (2H, m, CH$_2$-cyclopropyl), 0.04. (2H, m, CH$_2$-cyclopropyl).

e) R=normal-tert.butyl $^1$H-NMR (CDCl$_3$, 250 MHz, δ): 6.35, 6.12 (2H, AB, J=11.2 Hz, H-6 and H-7), 5.36 (1H, s broad, H-16), 5.29 (1H, s broad, H-19$_E$), 4.96 (1H, s broad, H-19$_Z$), 4.36 (1H, m, H-1), 4.11 (1H, s broad, H-3), 2.83 (1H, m, H-14), 1.12 (6 H, s, Me-26 and Me-27), 0.88 (9H, s, t-Bu), 0.68 (3H, s, Me-18).

f) R=normal-phenyl $^1$H-NMR (CDCl$_3$, 250 MHz, δ): 7.27–7.12 (5H, m, Ar), 6.35, 6.08 (2H, AB, J=11.2 Hz, H-6 and H-7), 5.55 (1H, m, H-16), 5.23 (1H, s broad, H-19$_E$), 4.97 (1H, s broad, H-19$_Z$), 4.39 (1H, m, H-1), 4.18 (1H, m, H-3), 2.71 (1H, m, H-14), 1.11 (6H, s, Me-26 and Me-27), 0.69 (3H, s, Me-18).

EXAMPLE 3

Preparation of intermediate 10 of general formula II

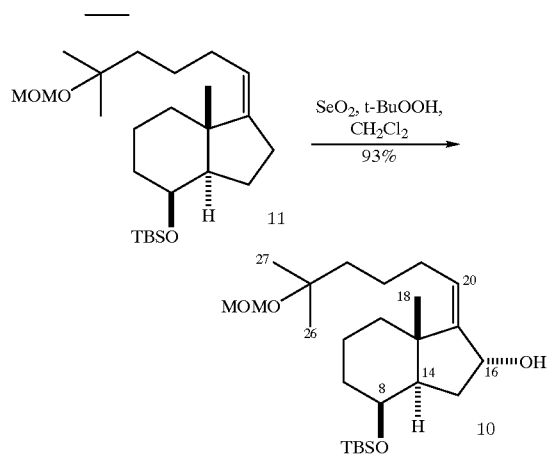

To a cooled (0° C.) suspension of 1.1. of freshly sublimed SeO$_2$ (10.3 mmol) in 30 ml dry CH$_2$Cl$_2$ under an argon atmosphere, was added 6.8 ml of a 3 M solution of t-BuOOH (20.5 mmol). The mixture was stirred for I hr followed by the addition of a solution of 5.7 g of compound 11(13.4 mmol) in 130 ml of dry CH$_2$Cl$_2$. After addition was completed, stirring was continued for 6 hrs at room temperature. The reaction was quenched by the addition of 50 ml of a 10% aqueous NaOH solution. The aqueous fase was extracted with CH$_2$Cl$_2$(3–25 ml). The combined organic layers were dried, filtered and concentrated at reduced pressure. The residue was purified by flash chromatography (eluent 10% EtOAC/hexane) resulting in 5.5 g of compound 10 as a colourless oil (93%, Rf=0.43; 20% EtOAc/hexane).

$^1$H-NMR (CDCl$_3$, 250 MHz, δ): 5.38 (1H, dt, J=7.4 Hz and 1.1 Hz, H-20), 4.69 (2H, s, OCH$_2$O), 4.44 (1H, d, J=6.0 Hz, H-16), 4.09 (1H, m, H-8), 3.36 (3H, s, MeO), 2.22–2.12 (3H, m, H-22 and H-14), 1.20 (6H, s, Me-26 and Me-27), 1.09(3H, s, Me-18), 0.88(9H, s, t-BuSi), 0.02(3H, s, Me$_2$Si), 0.01 (3H, s, Me$_2$Si).

We claim:

1. A method of preparing a 16-dehydro vitamin D compound of the formula I

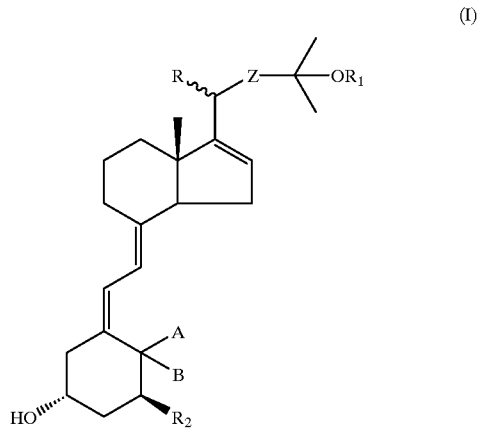

(I)

wherein

R has the epi-configuration or the normal configuration and represents straight or branched C$_{1-6}$-alkyl, C$_{2-6}$- alkenyl, $C_{3-6}$-cycloalkyl, or an aromatic group optionally substituted with halogen, $C_{1-3}$-alkyl or alkoxy, Z is a saturated or unsaturated straight hydrocarbon group or oxahydrocarbon group containing 3–6 C-atoms which may be 15 substituted with OH, F, alkyl ($C_{1-3}$) or cycloalkyl ($C_{3-5}$), $R_1$ is hydrogen or an hydroxy protecting group, $R_2$ is hydrogen or hydroxy, and A and B represent hydrogen or methyl, or together form the methylene group, characterised in that a compound of the formula II

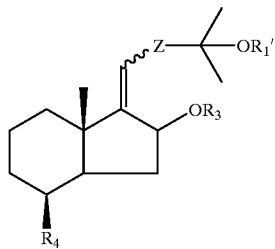

(II)

wherein Z has the above meaning, $R'_1$ is a hydroxy protecting group, $R_3$ is a carbamate group or trimethyl acetyl and $R_4$ is a protected hydroxy group ora group of the formula III

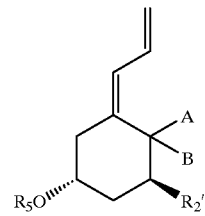

(III)

wherein A and B have the above meaning, $R_5$ is a hydroxy protecting group, and $R_2'$ is hydrogen or a hydroxy protecting group, is converted with a suitable cuprate reagent for introducing group R to a compound of the formula IV

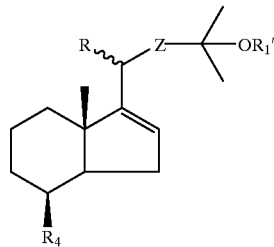

(IV)

wherein R, $R_1'$, Z and $R_4$ have the above meaning, followed by converting the obtained compound having formula IV into a compound having formula I.

* * * * *